United States Patent [19]

Lyle

[11] Patent Number: 5,814,323
[45] Date of Patent: Sep. 29, 1998

[54] COSMETIC COMPOSITION

[75] Inventor: Ian Gardner Lyle, Flintshire, United Kingdom

[73] Assignee: Lever Brothers Company, Division of Conopco, Inc., New York, N.Y.

[21] Appl. No.: 720,999

[22] Filed: Oct. 15, 1996

[30] Foreign Application Priority Data

Oct. 16, 1995 [GB] United Kingdom .................. 9521125

[51] Int. Cl.$^6$ ...................................................... A61K 7/00
[52] U.S. Cl. .............................. 424/401; 424/63; 424/701
[58] Field of Search ........................... 424/401, 63, 70.1; 514/772, 773

[56] References Cited

U.S. PATENT DOCUMENTS

| | | | |
|---|---|---|---|
| 4,048,338 | 9/1977 | Gerecht | 424/358 |
| 4,963,535 | 10/1990 | Sebag | 514/54 |
| 5,298,240 | 3/1994 | Schroder et al. | 424/70 |

FOREIGN PATENT DOCUMENTS

| | | |
|---|---|---|
| 217105 | 4/1987 | European Pat. Off. . |
| 550960 | 7/1993 | European Pat. Off. . |
| 1439244 | 6/1976 | United Kingdom . |
| 93/19159 | 9/1993 | WIPO . |

OTHER PUBLICATIONS

Internation Search Report in connection with the PCT Case No. EP 96/04087.
American Chemical Society Symposium Series, vol. 253, 1983, Washington USA, pp. 117–128, XP000,644,484, A. Bell: "Aqueous Solution Properties of a Fatty Dicarboxylic Acid Hydrotrope".
Journal of the American Oil Chemist Society, vol. 48, No. 3, 1971, pp. 113–115, XP 002,025,234, S. Fribert: "Solubilization of Triglycerides by Hydrotropic Interaction: Liquid Crystal Phases".
UK Search Report.

*Primary Examiner*—Thurman K. Page
*Assistant Examiner*—D. Faulkner
*Attorney, Agent, or Firm*—Ronald A. Koatz

[57] ABSTRACT

A process for reversibly applying a cosmetic composition to the skin or comprising: a) contacting the skin or hair with the cosmetic composition, the composition comprising at least one amphiphilic material which is capable of forming a water-insoluble liquid crystal phase of greater than one-dimensional periodicity and a cosmetic agent and b) when desired, removing the cosmetic composition by applying to the skin or hair a cleansing composition comprising a surface active agent and a hydrotrope capable of destroying the liquid crystal phase formed in a step a). An advantage of such a system is that the cosmetic agent is strongly adhered to the skin or hair when applied and can be effectively removed when desired.

2 Claims, No Drawings

COSMETIC COMPOSITION

The present invention relates to a process for applying a cosmetic agent to the skin and, when desired, removing it therefrom.

The need to formulate compositions which can affix cosmetic active agents to the skin and hair such that they are not readily or accidentally removed therefrom, such as by water or by rubbing the skin or hair, is well recognised. One such group of cosmetic agents are make-up products such as foundations, eyeshadows, blushers and mascara.

British Patent Specification No. 1 439 244 is concerned with formulating compositions and, in particular, cosmetic compositions containing an active component such that during use the active component is substantively fixed to the skin, i.e. it is adsorbed onto the skin surface and not readily removed therefrom such as by water.

Whilst in some instances it is preferred that a cosmetic agent is permanently applied to the skin, such as for example a skin cream containing active components such as alpha hydroxy acids, in other cases, such as for example for make-up, it is desirable that the cosmetic agent is non-permanently applied to the skin and can be removed by the wearer when desired.

For the latter group of cosmetic agents there is a balance between ensuring that the agent is strongly adhered to the skin, such that it cannot accidentally be removed therefrom, and enabling it to be effectively removed from the skin when desired.

We have now found a process for reversibly applying a cosmetic agent which involves forming a liquid crystal phase comprising the cosmetic agent.

Thus, according to the present invention there is provided a process for reversibly applying a cosmetic composition to the skin comprising the steps:
  a) contacting the skin with the cosmetic composition, the composition comprising at least one amphiphilic material which is capable of forming a water-insoluble liquid crystal phase of greater than one-dimensional periodicity and a cosmetic agent; and
  b) when desired, removing the cosmetic composition by applying to the skin a cleansing composition comprising a surface active agent and a hydrotrope capable of destroying the liquid crystal phase formed in step a).

It is to be understood in the context of the invention that "amphiphilic material" may include a mixture of materials, at least one of which is amphiphilic.

Water and certain organic substances can interact to form different structures of liquid crystal. An example of this teaching is to be found in "Biological Membranes" by D Chapman, Academic Press New York, 1968, Chapter 3, the content of which is incorporated herein by reference. Amongst the more defined liquid crystal structures that can be formed are cubic liquid crystal structures, which have a long-range periodicity in three dimensions, and hexagonal structures, which have a long-range periodicity in two dimensions.

It has been found that certain amphiphilic substances of the type described above (an amphiphilic substance by definition has both hydrophilic and hydrophobic portions in its structure), or mixtures of amphiphilic substances, have an appropriate relative insolubility in water enabling them to form the basis of skin or hair substantive cosmetic compositions. Preferably, the amphiphilic materials in accordance with the invention have a solubility in water of less than about 0.1% by weight (at 35° C.), more preferably less than about 0.05% by weight.

In addition, at certain concentrations of solution with water, these amphiphilic materials may pass through physical phases of one dimensional periodicity or less, such as a lamellar phase, or a simple liquid phase, in which they remain fairly fluid. These types of structures are thought not to be conducive to ensuring substantivity of the cosmetic agent to the skin or hair in the presence of water unless on contact with water they transform to a liquid crystal phase of greater than one-dimensional periodicity.

Preferred amphiphilic materials in accordance with the invention are those which form the most rigid liquid crystal structures (e.g. those with three-dimensional periodicity).

Conveniently, the structure of the amphiphilic materials can be determined by standard X-ray scattering techniques, such as those described in the reference "Biological Membranes" referred to above, and which will indicate the periodicity of any structure.

Preferred amphiphilic materials are those which form the most physically rigid liquid crystal at a temperature within the range 25° to 40° C., around the typical skin and hair surface temperatures.

A preferred category of amphiphilic materials comprises lipid substances, in particular lipids which may be found to occur naturally, for example in the human skin. Some examples of lipids which form effective amphiphilic materials according to the invention are glyceryl monooleate, optionally as a mixture with oleic acid, and a mixture of glyceryl monolaurate and oleic acid. When the amphiphilic material comprises a mixture of glyceryl monolaurate and oleic acid, preferably the ratio of glyceryl monolaurate to oleic acid is in the range from 3:2 to 4:1. Further examples of preferred lipid materials include glyceryl monolaurate in combination with any of oleyl alcohol, isostearyl alcohol or a mixture of isostearyl alcohol and stearyl alcohol; sodium oleate with oleic acid or oleyl alcohol; potassium oleate with oleic acid or oleyl alcohol; phospholipids such as lecithin and lysolecithin and their mixtures with oleic acid or oleyl alcohol.

Certain synthetic surfactants, such as mixtures of polyoxyethylene ethers, are also suitable amphiphilic materials according to the invention.

A further category of amphiphilic materials are polymer amphiphilic complexes, such as for example, a mixture of Merquat 100 (poly(dimethyl diallyl ammonium chloride)), and sodium dodecyl sulphate (SDS), in a equimolar mixture of Merquat 100 monomer: SDS. The resulting mixture is capable of forming a hexagonal liquid crystal structure on contact with water.

Yet another category of suitable amphiphilic materials according to the invention are block copolymer surfactants, for example sodium 10-$\Omega$-butyl [poly (dimethysiloxy) dimethyl silyl] decanoate.

If the amphiphilic material is, or comprises, glyceryl monooleate this has the added advantage that this material is absorbed by the skin, and in the process of doing so can absorb water which is drawn into the skin, thereby producing a moisturising effect. Furthermore, the use of glyceryl monolaurate is advantageous since this material has antimicrobial properties.

The amphiphilic material in accordance with the invention preferably comprises from 5 to 80 wt. %, most preferably 10 to 50% of the cosmetic composition.

The cosmetic agent is an agent which is desirably in contact with the skin or hair for a limited time typically either because the cosmetic agent itself has a limited lifetime or it leaves the skin or hair with an adverse feel e.g. a greasy feel after prolonged contact with the skin or hair.

Furthermore, the cosmetic agent may provide a benefit to skin or hair treated therewith i.e. it moisturises, conditions, protects and/or enhances the appearance or sensory properties of the skin or hair. Such cosmetic agents include i) make-up components such as pigments used in lipsticks, mascara, foundations, blushers, eyeshadows and the like;

ii) perfumes;

iii) sunscreens such as octyl methoxyl cinnamate (Parsol MCX) and butyl methoxy benzoylmethane (Parsol 1789);

iv) conditioning oils such as avocado oil, bergamot oil, coconut oil, collagen/lanolin oil, evening primrose oil, jojoba oil, mineral oil, soybean oil, petrolatum, polydecene and squalane;

v) waxes such as beeswax, paraffin wax, lanolin wax, polyethylene wax, spermaceti, carnauba wax, candelilla wax, petroleum wax, and ozokerite wax;

vi) and mixtures thereof.

Preferably the cosmetic agent will be present in the cosmetic composition at a level within the range 1 to 50%; most preferably 5 to 25 wt. %.

The cosmetic composition will preferably also comprise a carrier. The carrier is such that it assists in the formulation of the cosmetic composition but substantially evaporates when the composition is applied to the skin or hair. Examples of suitable materials include volatile silicone oils examples of which include cyclomethicone, as the trimer, tetramer or pentamer; and hexamethyldisiloxane (DC200 0.65 cs, ex Dow Corning); and isoparaffins such as branched hydrocarbons with 8 to 14 carbon atoms. The carrier will preferably be present in an amount of 10 to 95, most preferably 20 to 90 wt. % based on the cosmetic composition.

The cosmetic composition according to the invention may optionally comprise a structurant such as clay materials, for example Bentone; and hydrophobically modified hydrotalcites such as Gilugels ex Giulini Chemie. These hydrotalcites are, for example, aluminium magnesium hydroxide modified with fatty acids.

The cosmetic composition of the invention may also comprise optional components customarily present in formulations intended to be applied to the skin or hair. Typical of such optional components are preservatives, colourants, opacifiers, vitamins such as vitamin A and E, and vitamin alkyl esters and derivatives of alpha hydroxy acids such as materials of formula:

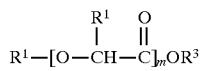

wherein $R^1$ is $C_pH_qN_rO_s$, where p is 0–20, q is 1–41, r is 0–3, and s is 0–3;

$R^2$ is $C_tH_u$ where t is 0–20 and u is 1–41;

$R^3$ is $C_vH_wN_xO_y$ where v is 0–20, w is 1–41, x is 0–3 and y is 0–3 or a metallic, ammonium or alkanolammonium anion; and m is 1–10.

Other optional components of the cosmetic composition include germicides such as synthetic antimicrobials, examples of which include salicylic acid; 3,4,4'-trichlorocarbanilide; 1,6-bis-(N p-chlorphenyl biguanido) hexane (Chlorhexidine); chlorhexidine gluconate; 2,4,4'-trichloro-2-hydroxydiphenyl ether (Irgasan DP300); imidazolidinyl urea; methyl, propyl, butyl, heptyl and benzyl p-hydroxy benzoate; 2-bromo-2-nitropropane-1,3 diol; nonyl phenol ethoxylate iodine complex; 2-phenoxylethanol; 3 dimethylol-5,5-dimethyl hydantoin; and natural antimicrobials such as willow extract; antioxidants such as butyl hydroxy toluene; and humectants such as glycerol, sorbitol, propylene glycol and polyethylene glycol.

The cosmetic compositions of the invention can take the form of solid, liquid, cream or lotion.

When the product is in the form of a liquid it may by dispensed directly onto the skin such as, for example, by a finger-operated pump spray or hand-operated squeeze spray delivering a finely divided spray or aerosol onto the skin.

Alternatively, when in the form of a liquid it may be applied to the skin by the use of an applicator, such as, for example, a cotton pad or in the case of mascara applied to eyelashes using a brush.

If the product is in the form of a cream it may be applied to the skin by massaging or rubbing it into the skin with the fingers.

The cleansing composition for use according to the invention comprises as its essential components a surface active agent, a hydrotrope and, in the case of liquid formulations, water.

The hydrotrope as herein defined is a water-soluble molecule which increases the solubility of the amphiphilic material in the aqueous phase. Thus, on contact with skin treated with a cosmetic composition in accordance with the invention, the liquid crystal phase is transformed to a micellar solution. The hydrotrope is preferably selected from short chain alcohols such as ethanol; short-chain diols such as propane 1,2-diol, propane 1,3-diol and ethane diol; polyethylene glycols such as PEG600; and urea; and is preferably present at a level of from 5 to 50 wt. %.

Whilst the cleansing composition may be in the form of a solid, preferably it will be in the form of an aqueous liquid.

The surface active agent is preferably selected from anionic, nonionic, cationic and amphoteric surface active agents and mixtures thereof.

One preferred anionic detergent is a fatty acyl isethionate of formula:

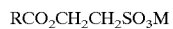

where R is an alkyl or alkenyl group of 7 to 21 carbon atoms and M is a solubilising cation such as sodium, potassium, ammonium or substituted ammonium. Preferably at least three quarters of the RCO groups have 12 to 18 carbon atoms and may be derived from coconut, palm or a coconut/palm blend.

Another preferred anionic detergent is alkyl ether sulphate of formula:

where R is an alkyl group of 8 to 22 carbon atoms, n ranges from 0.5 to 10 especially from 1.5 to 8, and M is a solubilising cation as before.

Other possible anionic detergents include alkyl glyceryl ether sulphate, sulphosuccinates, taurates, sarcosinates, sulphoacetates, alkyl phosphate, alkyl phosphate esters and acyl lactylate, alkyl glutamates and mixtures thereof.

Sulphosuccinates may be monoalkyl sulphosuccinates having the formula: $R^5O_2CCH_2CH(SO_3M)CO_2M$; and amido-MEA sulphosuccinates of the formula: $R^5CONHCH_2CH_2O_2CCH_2CH(SO_3M)CO_2M$; wherein $R^5$ ranges from $C_8$–$C_{20}$ alkyl, preferably $C_{12}$–$C_{15}$ alkyl and M is a solubilising cation.

Sarcosinates are generally indicated by the formula: $R^5CON(CH_3)CH_2CO_2M$, wherein $R^5$ ranges from $C_8$–$C_{20}$ alkyl, preferably $C_{12}$–$C_{15}$ alkyl and M is a solubilising cation.

Taurates are generally identified by the formula: $R^5CONR^6CH_2CH_2SO_3M$, wherein $R^5$ ranges from $C_8$–$C_{20}$ alkyl, preferably $C_{12}$–$C_{15}$. alkyl, $R^6$ ranges from $C_1$–$C_4$ alkyl, and M is a solubilising cation.

Harsh surfactants such as primary alkane sulphonate or alkyl benzene sulphonate will generally be avoided.

If the surface active agent comprises soap, the soap is preferably derived from materials with a $C_8$ to $C_{22}$ substantially saturated carbon chain and, preferably, is a potassium soap with a $C_{12}$ to $C_{18}$ carbon chain.

Suitable nonionic surface active agents include alkyl polysaccharides, lactobionamides, ethyleneglycol esters, glycerol monoethers, polyhydroxyamides (glucamide), primary and secondary alcohol ethoxylates, especially the $C_{8-20}$ aliphatic alcohols ethoxylated with an average of from 1 to 20 moles of ethylene oxide per mole of alcohol, and alkyl lactates of formula:

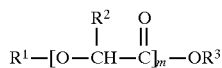

wherein $R^1$ is $C_xH_y$ where x and y are respectively numbers in the range 0 to 22 and 1 to 45; and $R^2$ is $C_xH_y$ where $x^1$ and $y^1$ are respectively numbers in the range 1 to 22 and 3 to 45; and m is 1 to 10.

A particularly preferred alkyl lactate is Crodamol LL (ex Croda), a lauryl lactate; or myristyl lactate.

Mixtures of any of the foregoing surface active agents may also be used.

The surface active agent is preferably present at a level of from 1 to 60 wt. %, preferably 5 to 30 wt. %.

It is also preferable that the composition includes from 0.5 to 15 wt. % of a cosurfactant agent with skin-mildness benefits, i.e. a synergistic mildness active. Suitable materials are zwitterionic detergents which have an alkyl or alkenyl group of 7 to 18 carbon atoms and comply with an overall structural formula:

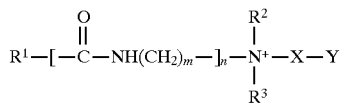

where $R^1$ is alkyl or alkenyl of 7 to 18 carbon atoms $R^2$ and $R^3$ are each independently alkyl, hydroxyalkyl or carboxyalkyl of 1 to 3 carbon atoms;

m is 2 to 4;

n is 0 or 1;

X is alkylene of 1 to 3 carbon atoms optionally substituted with hydroxyl; and

Y is $—CO_2^-$ or $—SO_3^-$.

Zwitterionic detergents within the above general formula include simple betaines of formula:

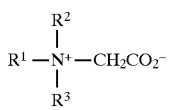

and amido betaines of formula:

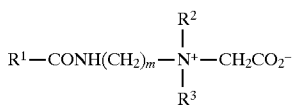

where m is 2 or 3.

In both formulae $R^1$, $R^2$ and $R^3$ are as defined previously. $R^1$ may, in particular, be a mixture of $C_{12}$ and $C_{14}$ alkyl groups derived from coconut so that at least half, preferably at least three quarters, of the group $R^1$ has 10 to 14 carbon atoms. $R^2$ and $R^3$ are preferably methyl.

A further possibility is a sulphobetaine of formula:

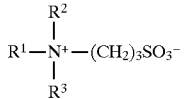

or

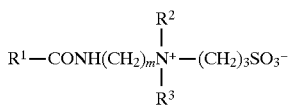

where m is 2 or 3, or variants of these in which $—(CH_2)_3SO_3^-$ is replaced by

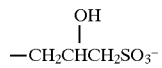

$R^1$, $R^2$ and $R^3$ in these formulae are as defined previously.

The cleansing composition may also optionally comprise a structurant and/or a thickener. Suitable materials include swelling clays, for example laponite; fatty acids and derivatives thereof and, in particular, fatty acid monoglyceride polyglycol ethers; cross-linked polyacrylates such as Carbopol (TM) (polymers available from Goodrich); acrylates and copolymers thereof, polyvinylpyrrolidone and copolymers thereof; polyethylene imines; natural gums including alginates, guar, xanthan and polysaccharide derivatives including carboxy methyl cellulose and hydroxypropyl guar; propylene glycols and propylene glycol oleates; salts such as sodium chloride and ammonium sulphate; sucrose esters; gellants; and mixtures thereof.

Of the clays, particularly preferred are synthetic hectorite (laponite) clay used in conjunction with an electrolyte salt capable of causing the clay to thicken. Suitable electrolytes include alkali and alkaline earth salts such as halides, ammonium salts and sulphates; and mixtures thereof.

Further examples of structurants and thickeners are given in the International Cosmetic Ingredient Dictionary, Fifth Edition, 1993, published by CTFA (The Cosmetic, Toiletry & Fragrance Association), incorporated herein by reference.

Other optional components of the cleansing composition include germicides such as synthetic antimicrobials, examples of which include salicylic acid; 3,4,4'-trichlorocarbanilide; 1,6-bis-(N p-chlorphenyl biguanido)

hexane (Chlorhexidine); chlorhexidine gluconate; 2,4,4'-trichloro-2-hydroxydiphenyl ether (Irgasan DP300); imidazolidinyl urea; methyl, propyl, butyl, heptyl and benzyl p-hydroxy benzoate; 2-bromo-2-nitropropane-1,3 diol; nonyl phenol ethoxylate iodine complex; 2-phenoxyethanol; 3 dimethylol-5,5-dimethyl hydantoin; and natural antimicrobials such as willow extract; antioxidants such as butyl hydroxy toluene; and humectants such as glycerol, sorbitol, propylene glycol and polyethylene glycol.

When the cleansing composition of the invention is in the form of a liquid it is preferably prepared by combining the hydrotrope with water and then dissolving the surface active agent into the resultant mixture.

When it is in the form of a solid product it is preferably prepared by forming a melt of the hydrotrope and surface active agent and then drying the mixture such as by air or vacuum drying. Thereafter, any optional components are added before the resultant mixture is milled, plodded and stamped.

Preferably the cosmetic composition and cleansing composition will be in the form of a cosmetic kit comprising:

a) a packaged composition comprising at least one amphiphilic material which is capable of forming a water-insoluble liquid crystal phase of greater than one-dimensional periodicity and a cosmetic agent; and b) in association therewith, a packaged composition comprising a surface active agent and a hydrotrope capable of destroying the liquid crystal phase of the cosmetic composition.

The invention also provides for the use in reversibly applying a cosmetic composition to the skin of:

a) a cosmetic composition comprising at least one amphiphilic material which is capable of forming a water-insoluble liquid crystal phase of greater than one-dimensional periodicity and a cosmetic agent; and b) a cleansing composition comprising a surface active agent and a hydrotrope capable of destroying the liquid crystal formed in step a) to remove the cosmetic composition when desired.

The invention will be further illustrated by reference to the following non-limiting examples.

EXAMPLES

Example 1

A water-proof mascara formulation (formulation 1A) was prepared by melting glycerol mono-oleate and then heating it to 50° C. before adding glycerol and water. The resulting viscous hexagonal phase was mixed. Thereafter, the pigment and preservatives were added and the mixture allowed to cool.

The clay thickener (Bentone 38) was mixed into $C_{10}$–$C_{11}$ isoparaffin at room temperature before adding to ethanol to form a stiff paste. This was then combined with the glycerol mono-oleate mixture and the resultant mixed thoroughly.

The resulting product was applied to an artificial eyelash using a spiral applicator brush.

The waterproof properties of the coating were tested by coating the mascara onto a clean glass microscope slide, allowing the volatile solvent to evaporate off and then holding the slide in warm, running tap water for 5 minutes. The mascara formulation was judged to be acceptable as it remained intact on the slide during the test.

A second water-proof mascara formulation (formulation 1B) was prepared using distilled unsaturated monoglycerides as a replacement for the glycerol mono-oleate using the same process as described for formulation 1A. The absence of glycerol resulted in the formulation drying quicker on the eyelash than formulation 1A. Using the test described above, the mascara was found to be substantive to water.

A further water-proof mascara formulation (formulation 1C) was prepared based on a combination of glycerol monolaurate and isostearyl alcohol by a similar route to that used for formulations 1A and 1B. The two amphiphilic materials were first warmed to melt and intimately mixed before adding water to form a stiff paste. It was tested using the test described above; the mascara was found to be substantive to water.

FORMULATIONS

|  | WT % | | |
| --- | --- | --- | --- |
|  | 1A | 1B | 1C |
| Glycerol monooleate, Nofable GO-901P (ex Nippon Oil & Fats | 11.60 | | |
| Distilled, unsaturated monoglycerides from sunflower oil, Dimodan LS (ex Grinsted Products) | | 13.28 | |
| Glycerol monolaurate Monomuls 90-L12 (ex Henkel) | | | 8.69 |
| Isostearyl alcohol Prisorine 3515 (ex Unichema) | | | 2.89 |
| Glycerol | 2.50 | | |
| Water | 2.50 | 3.32 | 5.02 |
| Ultramarine Blue (Reckitt's Colours) | 12.00 | 12.00 | 12.00 |
| Bentone 38 Quaternium-18 Hectorite (Rheox) | 10.00 | 10.00 | 10.00 |
| Ethanol | 2.50 | 2.00 | 2.50 |
| Preservative | 1.50 | 1.50 | 1.50 |
| Isoparaffin $C_{10-11}$, Isopar G (ex Exxon) | 57.50 | 58.0 | 57.50 |

Experiments were carried out to assess the ease of removal of the mascara 1A using various cleansing compositions. Glass microscope slides carrying the dried mascara were immersed in each of the cleansing formulations 1D–1F as detailed below. The make-up was readily removed by the inventive compositions 1D and 1F, but not by the comparative formulation 1E which contains no hydrotrope.

|  | 1D | 1E | 1F | 1G | 1H |
| --- | --- | --- | --- | --- | --- |
| Surface Active Agent | | | | | |
| Lauroyl lactylate | 10.0 | — | — | — | — |
| Alkylpolyglycoside (Oramix NS-10 ex Seppic) | — | 10.0 | 10.0 | — | — |
| PEG-8 $C_{12-18}$ alkyl ester (Xalifin 15 ex Vevy Europe) | — | — | — | 20.0 | 20.0 |
| PEG - 1500 monostearate | — | — | — | 5.0 | 5.0 |
| Hydrotrope | | | | | |
| Ethanol | 5.0 | — | 5.0 | 5.0 | — |
| Propane-1,2-diol | 10.0 | — | 10.0 | 10.0 | — |
| Triethanolamine to pH | 6.5 | — | — | — | — |
| Water | | | to 100 | | |

In a separate experiment, the regions of contact between deposits of mascara 1A, dried onto microscope slides, and droplets of the cleansing compositions 1D–1F, were examined under an optical microscope using crossed polars. The following results were found:

1D—On contacting mascara 1A, the sharp boundary between 1A and 1D disappeared, indicating the viscous liquid crystalline structure of the make-up had broken down, releasing the pigment particles.

1E—A distinct boundary layer with a birefringent liquid crystalline structure formed between mascara 1A and formulation 1E, which lacks the hydrotrope.

1F—When this aqueous cleansing formulation, comprising 1E with hydrotrope, was contacted with mascara 1A the boundary disappeared and no stable liquid crystalline interface formed.

In a separate test, a plastic disc was coated with mascara 1A and allowed to dry. Cleansing creams of formulations 1G and 1H (1H is a comparative formulation) were applied to a cotton pad and wiped over the mascara. The mascara was more effectively removed with cleansing composition 1G, which contained the hydrotrope, than with 1H.

Example 2

The following cream formulation was prepared:

|  | wt % |
|---|---|
| Glycerol monolaurate (Monomuls 90-L12) | 14.70 |
| Isostearyl alcohol (Prisorine 3515) | 4.90 |
| Water | 8.58 |
| Evening Primrose Oil | 14.08 |
| Perfume Oil | 1.41 |
| Hydrotalcite (Aluminium/Magnesium Hydroxide Palmitate) | 14.08 |
| Isoparaffin $C_{10}$–$C_{11}$ (Isopar G) | 42.25 |

The glycerol monolaurate, isostearyl alcohol and evening primrose oil were mixed together at 50° C., then water was added and the mixture allowed to cool to form the liquid crystalline base. The hydrotalcite, isoparaffin and perfume oil were first mixed together at room temperature, then combined with the liquid crystal base and mixed thoroughly. The resulting barrier cream, when applied to skin, resulted in a protective surface film which, in a sensory test, resisted removal by rinsing under running water and by washing with conventional soap and water, but was readily removed by cleansing composition 1D containing hydrotropes.

We claim:

1. A process for reversibly applying a cosmetic composition to the skin comprising the steps:

(a) first contacting the skin or hair with the cosmetic composition, the composition comprising; (i) at least one amphiphilic material which is capable of forming a water-insoluble liquid crystal phase of greater than one-dimensional periodicity when said composition is applied to the skin; and (ii) a cosmetic agent; and (b) subsequently removing the cosmetic composition by applying to the skin or hair a cleansing composition comprising a surface active agent and a hydrotrope capable of destroying the liquid crystal phase formed in step (a).

2. A cosmetic kit comprising:

(a) a packaged composition comprising; (i) at least one amphiphilic material which is capable of forming a water-insoluble liquid crystal phase of greater than one-dimensional periodicity when said composition is applied to the skin; and (ii) a cosmetic agent; and (b) in association therewith, a packaged composition comprising a surface active agent and a hydrotrope capable of destroying the liquid crystal phase.

* * * * *